(12) United States Patent
Wang et al.

(10) Patent No.: US 8,563,733 B2
(45) Date of Patent: Oct. 22, 2013

(54) PROCESS FOR THE PREPARATION OF ESOMEPRAZOLE AND SALTS THEREOF

(75) Inventors: Fan Wang, Hamilton (CA); Laura Kaye Montemayor, St. George (CA); Daqing Che, Brantford (CN); Stephen E. Horne, Burlington (CA)

(73) Assignee: Apotex Pharmachem Inc, Brantford (CA)

( * ) Notice: Subject to any disclaimer, the term of this patent is extended or adjusted under 35 U.S.C. 154(b) by 174 days.

(21) Appl. No.: 12/855,667

(22) Filed: Aug. 12, 2010

(65) Prior Publication Data

US 2010/0324298 A1 Dec. 23, 2010

Related U.S. Application Data

(60) Division of application No. 11/797,921, filed on May 9, 2007, now Pat. No. 7,786,309, which is a continuation-in-part of application No. 11/449,707, filed on Jun. 9, 2006, now abandoned.

(51) Int. Cl.
*C07D 401/12* (2006.01)
(52) U.S. Cl.
USPC .................................................. 546/273.7
(58) Field of Classification Search
USPC ..................................................... 546/273.7
See application file for complete search history.

(56) References Cited

U.S. PATENT DOCUMENTS

| | | | | |
|---|---|---|---|---|
| 4,045,563 A | * | 8/1977 | Berntsson et al. | 514/338 |
| 4,359,465 A | | 11/1982 | Ruwart | |
| 5,039,806 A | * | 8/1991 | Brandstram et al. | 546/273.7 |
| 5,840,910 A | * | 11/1998 | Souda et al. | 546/273.7 |
| 5,929,244 A | | 7/1999 | Von Unge | |
| 5,948,789 A | * | 9/1999 | Larsson et al. | 514/299 |
| 2004/0077869 A1 | | 4/2004 | Reddy et al. | |

FOREIGN PATENT DOCUMENTS

| | | |
|---|---|---|
| CA | 1265138 | 1/1990 |
| EP | 0005129 | 4/1981 |
| EP | 0124495 | 1/1987 |
| WO | WO 9208716 | 5/1992 |
| WO | WO 9532957 | 12/1995 |
| WO | WO 03089408 A2 | 10/2003 |
| WO | WO 03089408 A3 | 10/2003 |
| WO | WO 2007140608 | 12/2007 |

OTHER PUBLICATIONS

Pitchen P. et al.; An efficient asymmetric oxidation of sulfides to sulfoxides,; J. Am. Chem. Soc.; 1984;106:8188-8193.
Sigrist-Nelson K. et al.; Ro 18-5364, a potent new inhibitor of the gastric (H+ + K+)-ATPase.; Eur. J. Biochem.; 1987;166:453-459.
Zhao S.H. et al.; Asymmetric oxidation of sulfides mediated by chiral titanium complexes: Mechanistic and synthetic aspects.; Tetrahedron;1987;43(21):5135-5144.

* cited by examiner

*Primary Examiner* — Patricia L Morris

(57) ABSTRACT

A novel process for the preparation of omeprazole and its enantiomers, such as esomeprazole, as well as the preparation of related 2-(2-pyridinylmethyl-sulphinyl)-1H-benzimidazoles, including pantoprazole, lansoprazole and rabeprazole, as recemates or single enantiomers, and their alkali or alkaline salts has been developed. The novel process involves the surprising discovery that protection of the free-base benzimidazole sulfoxide (e.g. omeprazole or esomeprazole), by reaction with an alkyl, aryl or aralkyl chloroformate following oxidation of the corresponding sulfide, eliminates the need for its direct isolation. Subsequent removal of the protecting group with a solution of alkali or alkaline earth alkoxide in a C1-C4 alcohol directly provides the corresponding salt. By eliminating the need to handle the free-base benzimidazole sulfoxide, this advantageous procedure provides increased chemical yields over processes described in the art.

1 Claim, No Drawings

PROCESS FOR THE PREPARATION OF ESOMEPRAZOLE AND SALTS THEREOF

CROSS-REFERENCES TO RELATED APPLICATIONS

This application is a divisional application of U.S. non-provisional patent application Ser. No. 11/797,921, filed on May 9, 2007 which is a continuation-in-part application of U.S. non-provisional patent application Ser. No. 11/449,707, filed on Jun. 9, 2006, now abandoned, the entire disclosures of which are herein incorporated by reference for all purposes.

FIELD OF THE INVENTION

The present invention relates to a novel process for preparing esomeprazole, or the enantioselective preparation of single enantiomers of related 2-(2-pyridinylmethyl-sulphinyl)-1H-benzimidazoles, including pantoprazole, lansoprazole and rabeprazole, and pharmaceutically acceptable alkali and alkaline earth salts thereof. The present invention may also be used as an alternative method of preparation for racemic 2-(2-pyridinylmethyl-sulphinyl)-1H-benzimidazoles, including omeprazole, pantoprazole, lansoprazole, and rabeprazole, when achiral oxidation reactions are used.

BACKGROUND OF THE INVENTION

Esomeprazole magnesium 1, the (S)-enantiomer of the proton pump inhibitor omeprazole, was developed by AstraZeneca as a second-generation of Prilosec®, and is currently marketed as Nexium®.

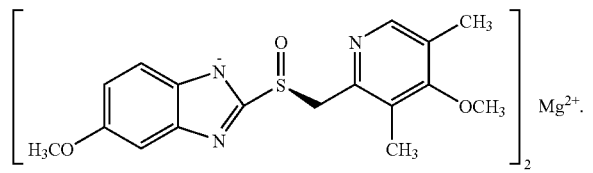

Esomeprazole is effective for the treatment of conditions such as stomach and duodenal ulcers, gastroesophageal reflux disease, and Zollinger-Ellison syndrome. Its mode of action is as a proton pump inhibitor, thereby reducing gastric acid levels in the stomach, permitting the stomach and esophagus to heal.

Chemically known as (T-4)-Bis[5-methoxy-2-[(S)-[(4-methoxy-3,5-dimethyl-2-pyridinyl)methyl]sulfinyl]-1H-benzimidazolato]magnesium (1), esomeprazole magnesium can be prepared through processes known in the art.

Sigrist-Nelson et al. (*Eur. J. Biochem.* 1987, 166, 453-459) prepared optically active benzimidazole sulfoxides, with structural similarities to omeprazole, using the procedure of Pitchen et al. (*J. Am. Chem. Soc.* 1984, 160, 8188-8193). While the enantiomeric excesses reported were lower than those achieved by Pitchen et al., later work (Zhao, S. H. et al. *Tetrahedron* 1987, 43, 5135-5144) demonstrated that changes to the reaction conditions could offer improved results.

For instance, U.S. Pat. No. 5,948,789 discloses a process that involves an asymmetric oxidation of sulfide 2 with an enantiomeric excess of 87%. The optical purity of sulfoxide 1a could be then improved via recrystallization of the sodium analog of 1. However, this process suffers from various deficiencies including low (less than 50% on average) chemical yield.

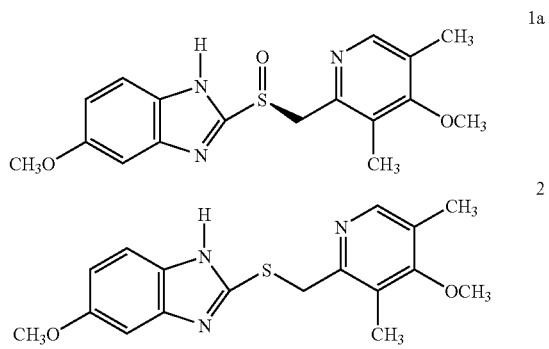

Another method to prepare optically pure sulfoxide 1 employs resolution of a racemic mixture of the sulfoxide. For instance, WO 95/32957 teaches a method to obtain optically pure sulfoxide 1a in neutral form by separation of a diastereomeric mixture by chromatography followed by removal of the derivatizing agent. This process involves multiple steps and is not practical for industrial scale.

WO 92/08716 discloses a process to prepare enantiomerically pure pantoprazole, a structurally similar antiulcer drug developed by BYK GmbH, and enantiomerically pure (+)-omeprazole, which could also be adapted for esomeprazole (1a). This process is similar to WO '957 in which different diastereomers of the sulfoxide derivatives are separated by re-crystallization. Again this process requires multiple steps resulting in a low yield.

U.S. Pat. No. 5,929,244 by Astra reveals a process for the purification of an enantiomerically enriched sulfoxide mixture by re-crystallization in various organic solvents. This process is easy to operate but requires several re-crystallizations to achieve the requisite enantiomeric purity for use as a pharmaceutical.

In WO 03/089408, Sun Pharmaceutical discloses a similar process to US '789 in which chiral methyl mandelate is used followed by formation of a chiral Ti(IV) complex. The process suffers the same drawbacks as before, for example, additional chemical operations and low (less than 50%) yield.

US 2004/077869 discloses a novel process to produce optically pure sulfoxide 1a in neutral form in which the racemic or enantiomerically enriched sulfoxide is resolved by formation of a Ti(IV) complex using a Ti(OiPr)$_4$/diethyl D-tartrate/L-mandelic acid system. This multi-step process is relatively complex, laborious, and low yielding.

U.S. Pat. No. 5,039,806, by A B Hassle, discloses the racemic preparation of derivatives 3 by either acylation of the sulfoxide or acylation of the corresponding sulfide, followed by oxidation. However, when compared to the present process, the chemical yields are low.

Therefore, an object of the invention is to provide a facile and commercially viable process to produce esomeprazole (1a), and its pharmaceutically acceptable alkali and alkaline earth salts, which overcomes some of the disadvantages of the prior art by providing an increased yield and a process that avoids isolating the unstable esomeprazole as an intermediate.

Similarly, an object of the invention is to provide a facile and commercially viable process to produce omeprazole, and its pharmaceutically acceptable alkali and alkaline earth salts, which overcomes some of the disadvantages of the prior art by providing an increased yield and a process that avoids isolating the unstable omeprazole as an intermediate.

EP 0 005 129, by A B Hassle, discloses the preparation of omeprazole, and other related benzimidazoles, via oxidation of the corresponding sulfide with meta-chloroperbenzoic acid. This procedure results in the isolation of the free-base of omeprazole.

EP 0 124 495, by A B Hassle, discloses the preparation of various salts of omeprazole, including sodium and magnesium, however, the process utilizes the free-base of omeprazole, making it unattractive for use on an industrial scale.

Further and other objects of the invention will become apparent to those skilled in the art when considering the following summary of the invention and a more detailed description of the preferred embodiments contained herein.

SUMMARY OF THE INVENTION

It has been unexpectedly and surprisingly discovered that esomeprazole could be prepared using a straightforward, robust and scalable process that is convenient and effective. This novel process is depicted in Scheme 1 for the preparation of esomeprazole (1a) and its alkali metal and alkaline earth salts (1b). It has also been discovered that if a solution of an alkali metal alkoxide or alkaline earth metal alkoxide in a C1 to C4 alkyl alcohol is employed in the decarbamoylation step, the corresponding salt of esomeprazole can be prepared directly. In this instance, it is advantageous in that it avoids isolation and handling of the esomeprazole free base, thus leading to an enhanced chemical yield over procedures described in the art.

In one aspect of the invention there is provided a process to prepare esomeprazole or alkali and alkaline earth metal salts thereof. The said process comprises the following steps:
(1) enantioselectively oxidizing the prochiral sulfide 2, 2-[2-(3,5-dimethyl-4-methoxypyridyl)methylthio]-5-methoxy-benzimidazole to the corresponding sulfoxide using an asymmetric oxidation method,
(2) acylating with an alkyl, aryl, or aralkyl chloroformate at the N-atom of the benzimidazole ring to produce enantiomerically-enriched derivatives 3 (R=alkyl, aryl or aralkyl),
(3) mixing the enantiomerically-enriched derivatives 3 with:
  (a) a C1 to C4 alkyl alcohol, or
  (b) a solution of an alkali metal alkoxide in a C1 to C4 alkyl alcohol, or
  (c) a solution of an alkaline earth metal alkoxide in a C1 to C4 alkyl alcohol, and,
(4) isolating the corresponding esomeprazole in its neutral form by precipitation by concentration and/or addition of an anti-solvent(s) or spray drying; or isolation as an alkali metal salt or an alkaline earth metal salt by precipitating by concentration and/or addition of an anti-solvent(s) or spray drying the solution.

In another aspect of the invention the N-atom of the benzimidazole ring of the enantiomerically enriched sulfoxide is protected with a protecting group selected from alkoxycarbonyl, aryloxycarbonyl or aralkoxycarbonyl to form enantiomerically-enriched N-protected derivatives 3. Preferably, the protecting group is tert-butoxycarbonyl or benzyloxycarbonyl.

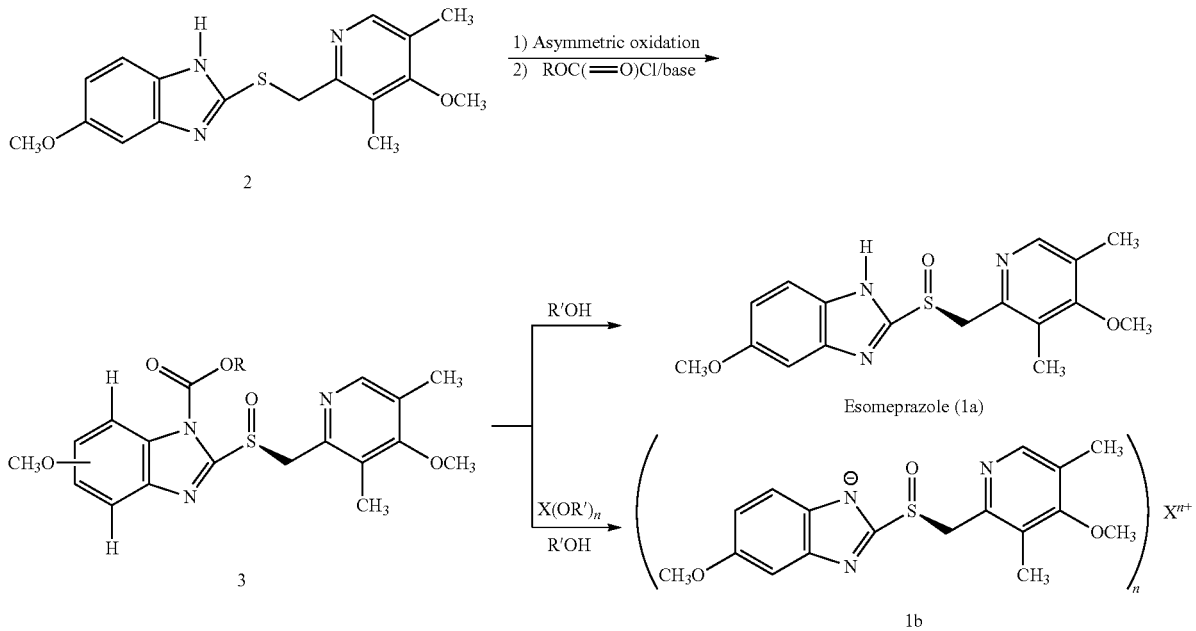

In yet another aspect of the invention there are provided the enantiomerically-enriched N-protected compounds 3.

In yet another aspect of the invention there are provided esomeprazole or its alkali or alkaline earth metal salts from the enantiomerically-enriched compounds of formula 3 in a one-pot manner using a C1 to C4 alkyl alcohol or together with an alkali metal alkoxide, or with an alkaline earth metal alkoxide. Preferably the alcohol is methanol, ethanol or iso-propanol. More preferably the alcohol is methanol. Preferably the alkali metal or alkaline earth salt is magnesium, sodium, potassium, lithium, or calcium. More preferably, the alkali metal or alkaline earth salt is sodium or magnesium.

In yet another aspect of the invention there are provided solutions containing esomeprazole in a C1 to C4 alkyl alcohol by directly adding the derivatives 3 to the C1 to C4 alkyl alcohol. Preferably the alcohol is methanol, ethanol or iso-propanol. More preferably the alcohol is methanol.

In yet another aspect of the invention there is provided a solution containing esomeprazole alkali metal salt in a C1 to C4 alkyl alcohol by directly adding the enantiomerically-enriched derivatives 3, preferably in a quantity of about 1 mole of esomeprazole per mole of alkali metal, to a solution of alkali metal alkoxide in a C1 to C4 alkyl alcohol. Preferably the alcohol is methanol, ethanol or iso-propanol. More preferably the alcohol is methanol. Preferably the alkali metal or alkaline earth salt is magnesium, sodium, potassium, lithium, or calcium. More preferably, the alkali metal or alkaline earth salt is sodium or magnesium.

In yet another aspect of the invention there are provided solutions containing esomeprazole alkaline earth metal salt in a C1 to C4 alkyl alcohol by directly adding the enantiomerically-enriched derivatives 3, preferably in a quantity of about 2 moles of esomeprazole per mole of alkaline earth metal, to solutions of alkaline earth metal alkoxide in a C1 to C4 alkyl alcohol. Preferably the alcohol is methanol, ethanol or iso-propanol. More preferably the alcohol is methanol. Preferably the alkali metal or alkaline earth salt is magnesium, sodium, potassium, lithium, or calcium. More preferably, the alkali metal or alkaline earth salt is sodium or magnesium.

In yet another aspect of the invention there is provided esomeprazole or its salts by adding anti-solvents to an optionally concentrated alcoholic solutions containing esomeprazole, esomeprazole alkali metal salt or esomeprazole alkaline earth metal salt. These anti-solvents include C1 to C3 alkyl acetates such as ethyl acetate and C4 to C8 alkyl ethers such as methyl t-butyl ether (MTBE), diethyl ether and diisopropyl ether, and a C6 to C9 hydrocarbon such as hexane of heptane, or mixtures thereof. The most preferable anti-solvents are ethyl acetate and MTBE. Preferably the alcohol is methanol, ethanol or iso-propanol. More preferably the alcohol is methanol. Preferably the alkali metal or alkaline earth salt is magnesium, sodium, potassium, lithium, or calcium. More preferably, the alkali metal or alkaline earth salt is sodium or magnesium.

In yet another aspect of the invention there is provided a simple, scalable, and industrially applicable process that provides esomeprazole in high optical yield and a higher chemical yield than is currently available in the art.

In yet another aspect of the invention there are provided processes for the preparation of amorphous esomeprazole or its salts.

Owing to the structural similarities of other benzimidazoles sulfoxides, such as lansoprazole (4), pantoprazole (5) and rabeprazole (6), among others, each of which contains a chiral centre about the sulfur atom,

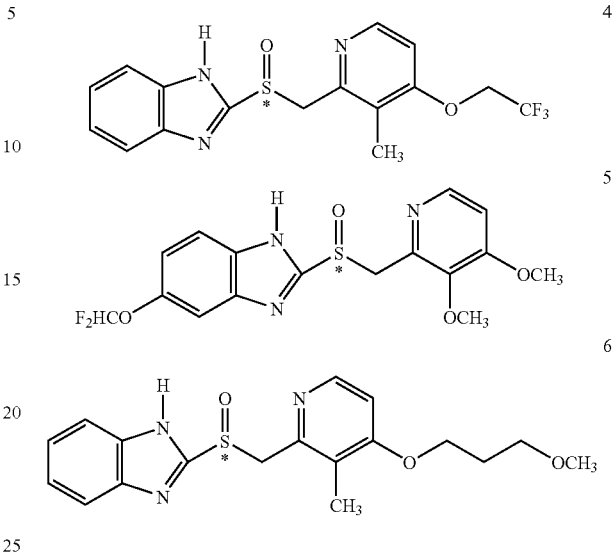

a further aspect of the invention would be the use of the above processes in the preparation either optical isomer of compounds of formula (I):

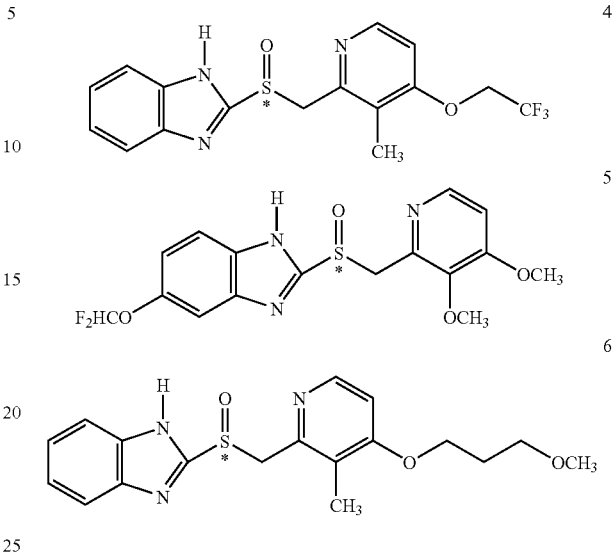

wherein
ring A is a benzene ring optionally having 1 to 3 substituent(s), which may be the same or different, are each independently selected from (a) a halogen atom, (b) a cyano, (c) a nitro, (d) an alkyl optionally having 1 to 3 substituent(s) selected from a halogen atom, a $C_{1-6}$ alkoxy, a $C_{1-6}$ alkoxy carbonyl and a carbamoyl, (e) an alkoxy optionally having 1 to 3 substituent(s) selected from a halogen atom, a $C_{1-6}$ alkoxy, a $C_{1-6}$ alkoxycarbonyl and a carbamoyl, (f) an aryl, (g) an aryloxy, (h) an acyl, (i) an acyloxy and (j) a 5- to 10-membered heterocyclic group, $R^1$, $R^2$ and $R^3$ are each a hydrogen atom; an alkyl group optionally having 1 to 3 substituent(s) selected from a halogen atom, a $C_{1-6}$ alkoxy, a $C_{1-6}$ alkoxycarbonyl and a carbamoyl; an alkoxy group optionally having 1 to 3 substituent(s) selected from a halogen atom, a $C_{1-6}$ alkoxy, a $C_{1-6}$ alkoxycarbonyl and a carbamoyl; or a di-$C_{6-14}$ arylamino, and

*is an asymmetric center, and their corresponding pharmaceutically acceptable alkali and alkaline earth metal salts.

As would be understood by the person skilled in the art, a chiral oxidation process, such as the one described in U.S. Pat. No. 5,948,789, may be used to produce a product consisting of either optical isomer depending on the chirality of the chiral auxiliary used. As such, a further aspect of the invention is a process that would allow for the preparation of either optical isomer of the desired benzimidazole, for example, (R)- or (S)-omeprazole.

A further aspect of the present invention is the use of the oxidation/protection/deprotection process in the preparation of racemic mixtures of 2-(2-pyridinylmethyl-sulphinyl)-1H-benzimidazoles such as omeprazole (see Scheme 2), pantoprazole, lansoprazole and rabeprazole or other compounds of Formula (I). Under these circumstances the procedure described below is employed. One example of such an achiral oxidation process would utilize meta-perchlorobenzoic acid as has been previously described in the art (EP 0 005 129).

aralkoxycarbonyl to form racemic N-protected derivatives 7. Preferably, the protecting group is tert-butoxycarbonyl or benzyloxycarbonyl.

In yet another aspect of the invention there are provided omeprazole or its alkali or alkaline earth metal salts from the racemic compounds of formula 7 in a one-pot manner using a C1 to C4 alkyl alcohol or together with an alkali metal alkoxide, or with an alkaline earth metal alkoxide. Preferably the alcohol is methanol, ethanol or iso-propanol. More preferably the alcohol is methanol. Preferably the alkali metal or alkaline

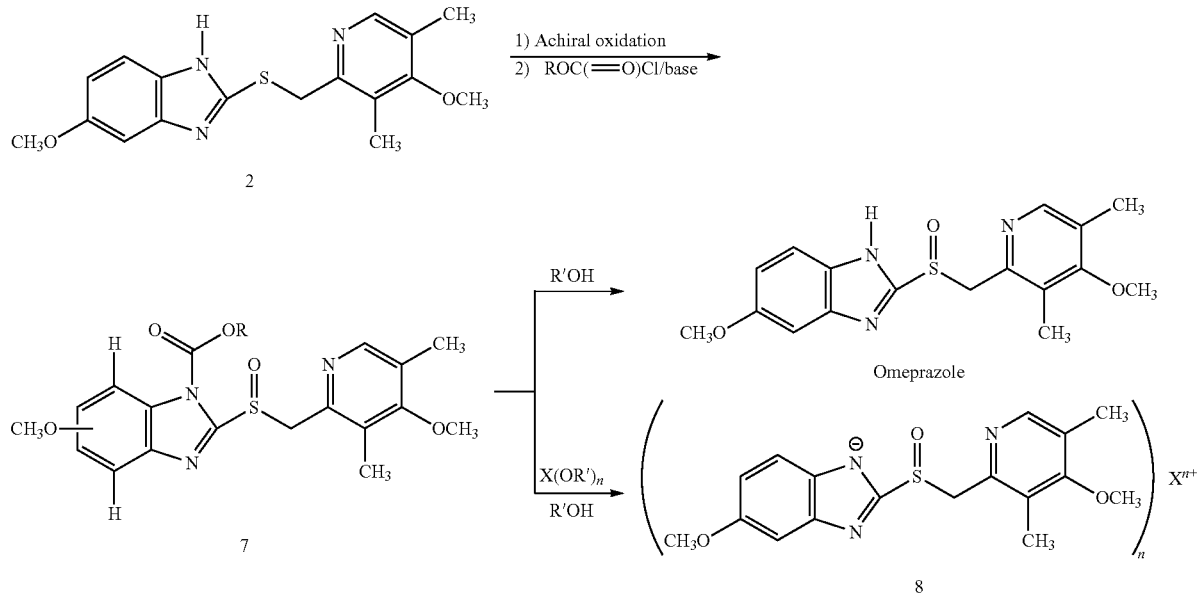

Scheme 2

$X = Li^+, Na^+, K^+, Ca^{2+}, or Mg^{2+}$
R = alkyl, aryl or aralkyl
R' = C1-C4 alkyl
n = 1 or 2

The said process comprises the following steps where the desired product is omeprazole:
(1) oxidizing the sulfide 2, 2-[2-(3,5-dimethyl-4-methoxy-pyridyl)methylthio]-5-methoxy-benzimidazole to the corresponding sulfoxide using a suitable oxidation method,
(2) acylating with an alkyl, aryl, or aralkyl chloroformate at the N-atom of the benzimidazole ring to produce derivatives 7 (R=alkyl, aryl or aralkyl),
(3) mixing the derivatives 7 with:
(a) a C1 to C4 alkyl alcohol, or
(b) a solution of an alkali metal alkoxide in a C1 to C4 alkyl alcohol, or
(c) a solution of an alkaline earth metal alkoxide in a C1 to C4 alkyl alcohol, and,
(4) isolating the corresponding omeprazole in its neutral form by precipitation by concentration and/or addition of an anti-solvent(s) or spray drying; or isolation as an alkali metal salt or an alkaline earth metal salt 8 by precipitating by concentration and/or addition of an anti-solvent(s) or spray drying the solution.

In another aspect of the invention the N-atom of the benz-imidazole ring of the sulfoxide is protected with a protecting group selected from alkoxycarbonyl, aryloxycarbonyl or earth salt is magnesium, sodium, potassium, lithium, or calcium. More preferably, the alkali metal or alkaline earth salt is sodium or magnesium.

In yet another aspect of the invention there are provided solutions containing omeprazole in a C1 to C4 alkyl alcohol by directly adding the derivatives 7 to the C1 to C4 alkyl alcohol. Preferably the alcohol is methanol, ethanol or iso-propanol. More preferably the alcohol is methanol.

In yet another aspect of the invention there is provided a solution containing omeprazole alkali metal salt in a C1 to C4 alkyl alcohol by directly adding the racemic derivatives 7, preferably in a quantity of about 1 mole of omeprazole per mole of alkali metal, to a solution of alkali metal alkoxide in a C1 to C4 alkyl alcohol. Preferably the alcohol is methanol, ethanol or iso-propanol. More preferably the alcohol is methanol. Preferably the alkali metal or alkaline earth salt is magnesium, sodium, potassium, lithium, or calcium. More preferably, the alkali metal or alkaline earth salt is sodium or magnesium.

In yet another aspect of the invention there are provided solutions containing omeprazole alkaline earth metal salt in a C1 to C4 alkyl alcohol by directly adding the racemic derivatives 7, preferably in a quantity of about 2 moles of omeprazole per mole of alkaline earth metal, to solutions of alkaline earth metal alkoxide in a C1 to C4 alkyl alcohol. Preferably the alcohol is methanol, ethanol or iso-propanol. More preferably the alcohol is methanol. Preferably the alkali metal or alkaline earth salt is magnesium, sodium, potassium, lithium, or calcium. More preferably, the alkali metal or alkaline earth salt is sodium or magnesium.

In yet another aspect of the invention there is provided omeprazole or its salts by adding anti-solvents to an optionally concentrated alcoholic solutions containing omeprazole, omeprazole alkali metal salt or omeprazole alkaline earth metal salt. These anti-solvents include C1 to C3 alkyl acetates such as ethyl acetate and C4 to C8 alkyl ethers such as methyl t-butyl ether (MTBE), diethyl ether and diisopropyl ether, and a C6 to C9 hydrocarbon such as hexane of heptane, or mixtures thereof. The most preferable anti-solvents are ethyl acetate and MTBE. Preferably the alcohol is methanol, ethanol or iso-propanol. More preferably the alcohol is methanol. Preferably the alkali metal or alkaline earth salt is magnesium, sodium, potassium, lithium, or calcium. More preferably, the alkali metal or alkaline earth salt is sodium or magnesium.

In yet another aspect of the invention there is provided a simple, scalable, and industrially applicable process that provides omeprazole.

In yet another aspect of the invention there are provided processes for the preparation of amorphous omeprazole or its salts.

DETAILED DESCRIPTION OF THE INVENTION

The preparation of 3 is typically achieved by the enantioselective oxidation of sulfide 2 by any known method in the art, such as the procedure described in U.S. Pat. No. 5,948, 789, followed by reaction with an alkyl, aryl or aralkyl chloroformate in the presence of a base, such as triethylamine to form crystalline compounds 3. Surprisingly, it was discovered that derivatives of 3 were readily isolable and purifiable, making the process efficient and practical for industrial scale.

The reaction of the sulfoxide intermediate with the alkyl, aryl or aralkyl chloroformate is achieved in a suitable organic solvent, most preferably a C1 to C3 chlorinated hydrocarbon such as dichloromethane or a C3 to C6 dialkyl ketone such as methyl isobutyl ketone. This reaction is performed at about −5 to about 30° C. and in the presence of an alkylamine base such as triethylamine. The stoichiometry of both the base and the chloroformate reagent is about 1.0 to 3.0 equivalents per equivalent of 2. The products 3 are extracted into a suitable organic solvent, such as ethyl acetate or another C3 to C6 alkyl ester, and precipitated by concentration of the organic solvent and/or addition of an anti-solvent. Examples of suitable anti-solvents include C6 to C9 hydrocarbons such as hexane or heptane. The most preferred anti-solvent is heptane.

Preferred chloroformates for use in the formation of 3 would be comprised of substituted or unsubstituted C1-C6 alkyl groups, substituted or unsubstituted C6-C9 aryl groups, or unsubstituted C7-C10 aralkyl groups. More preferred chloroformates would be comprised of benzyl or tert-butyl groups.

In another aspect of the invention, it has been found that when compounds 3 are treated with a C1 to C4 alkyl alcohol such as methanol, surprisingly, the N-protecting group is easily removed. After concentrating the alcoholic solution and/or addition of an anti-solvent, pure esomeprazole is precipitated and isolated by filtration.

It has been also found that the above process is also suitable for preparing alkali or alkaline earth salts of esomeprazole. Thus, the N-protected compounds 3 are treated with a solution of alkali or alkaline earth metal alkoxide in a C1 to C4 alkyl alcohol. The most preferred alcohol is methanol. The esomeprazole salt is isolated by concentration of the solution followed by the optional addition of an anti-solvent and/or by spray drying.

The esomeprazole salts prepared by this process can be any pharmaceutically acceptable alkali or alkaline earth metal salts. Preferably, the counter-ion would be an alkali or alkaline earth metal, selected from one of Li, Na, K, Ca or Mg. Most preferably the alkali or alkaline earth metal would be selected from sodium or magnesium, with the most preferable amount of the alkali or alkaline earth metal alkoxide being about 1 or 0.5 equivalents, respectively, relative to esomeprazole. The reaction temperature is from about −20° C. to refluxing temperature, preferably 0 to 25° C. Preferred C1 to C4 alkyl alcohols include methanol, ethanol, iso-propanol, n-propanol, and n-butanol, with the most preferred alcohol being methanol.

If a desired polymorph or amorphous form needs to be prepared, a person skilled in the art could make it accordingly. For example, if an amorphous form of the salt is required, an anti-solvent or anti-solvents could be added into the reaction mixture to precipitate the product in its amorphous form. The anti-solvents are organic solvents such as C4 to C8 alkyl ethers and C1 to C3 alkyl acetates, but not limited as such, in which the product has limited solubility. Similarly, other polymorphs known in the prior art can be prepared accordingly.

The following non-limiting examples further illustrate the manner of carrying out the inventive process described herein.

Example 1

Preparation of (S)-5/6-methoxy-1-benzyloxycarbonyl-2-[[(4-methoxy-3,5-dimethyl-2-pyridinyl)methyl]sulfinyl]-1H-benzimidazole To a solution of 2-[2-(3,5-dimethyl-4-methoxypyridyl) methylthio]-5-methoxy-benzimidazole 2 (10 g) in 50.0 mL toluene under an inert atmosphere, was added (D)-diethyl tartrate (2.75 g). The mixture was heated to 50-55° C. and stirred for 30 minutes. Titanium (IV) isopropoxide (1.73 g) was added and the temperature maintained at 50-55° C. for an additional 60 minutes. The reaction mixture was cooled to 0-5° C. whereupon diisopropylethylamine (1.33 g) and 80% cumene hydroperoxide (6.93 g) were added while keeping the temperature below 10° C. The reaction mixture was stirred at 0-10° C. for 2-4 hours until the reaction was complete. The reaction mixture was warmed to room temperature, filtered through Celite™ and extracted with 12-14% ammonium hydroxide. The aqueous and methyl isobutyl ketone (MIBK, 30 mL) phases were cooled to 0-5° C. The pH was adjusted to 7.3 to 7.8 with acetic acid and phases were separated. The aqueous phase was extracted with MIBK. The combined organic phases were washed with brine and vacuum distilled to 40 mL to give a solution of (S)-(−)-5-methoxy-2-[[4-methoxy-3,5-dimethyl-2-pyridinyl)methyl] sulfinyl]-1H-benzimidazole in MIBK. The sulfoxide solution was diluted with dichloromethane (30 mL) and triethylamine (4.61 g). The mixture was cooled to 0-10° C. and 95% benzyl chloroformate (6.0 g) was added while keeping the temperature below 10° C. After stirring for 1-4 hours, water (30 mL) and ethyl acetate (30 mL) were added. The phases were separated and the aqueous phase was extracted with ethyl acetate. The combined organic phases was washed with brine and saturated sodium bicarbonate, vacuum distilled to 30 mL and filtered through Celite™. The filtrate was stirred while 80 mL of heptanes was added dropwise whereupon the suspension was cooled to 0-5° C. and maintained at this temperature for 1-2 hours. The suspension was filtered, washed with heptanes/ethyl acetate (4/1) and dried under vacuum at room temperature to afford (S)-5/6-methoxy-3-benzyloxycarbonyl-2-[[4-methoxy-3,5-dimethyl-2-pyridinyl)-methyl]sulfinyl]-1/H-benzimidazole. Weight: 11.5 g. Purity: 99% by HPLC. Chiral purity: 99.5% (S-form) by HPLC. Ratio of 5- and 6-methoxy products: ~1:1. The analytical data were consistent with the assigned structure.

$^1$H-NMR (400 MHz, CDCl3):

5-Methoxy isomer

δ/ppm=2.18 (3H, s), 2.32 (3H, s), 3.73 (3H, s), 3.76 (3H, s), 4.67 (2H, dd, J=13, 38 Hz), 5.54 (2H, s), 6.95-7.01 (1H, m), 7.38 (1H, d, J=2 Hz), 7.40-7.43 (2H, m), 7.47-7.59 (2H, m), 7.68 (1H, d, J=9 Hz), 8.05 (1H, s);

6-Methoxy isomer

δ/ppm=2.18 (3H, s), 2.32 (3H, s), 3.73 (3H, s), 3.83 (3H, s), 4.67 (2H, dd, J=13, 38 Hz), 5.53 (2H, s), 6.95-7.01 (1H, m), 7.29 (1H, d, J=2 Hz), 7.40-7.43 (2H, m), 7.47-7.59 (2H, m), 7.75 (1H, d, J=9 Hz), 8.05 (1H, s).

Example 2

Preparation of Amorphous Esomeprazole Magnesium Salt (1)

Magnesium metal (0.26 g) was added to methanol (60 mL) and stirred at room temperature for 3-4 hours. To the mixture was added (S)-5/6-methoxy-3-benzyloxycarbonyl-2-[[4-methoxy-3,5-dimethyl-2-pyridinyl)-methyl]sulfinyl]-1H-benzimidazole (10 g, ~1:1 of 5- and 6-methoxy compounds) in portions. After stirring for 20-30 minutes the methanol was evaporated to a small volume and ethyl acetate was added, which caused precipitation. The damp cake obtained by filtration was pulped in ethyl acetate for 2-3 hours. The cake obtained by filtration was vacuum-dried to afford optically pure esomeprazole magnesium salt. X-ray powder diffraction pattern demonstrated the amorphous nature of the product. Weight: 7.1 g (75% overall yield). Purity: 99.3% by HPLC. Chiral purity: 99.2% (S-form) by HPLC. Mg content: 3.4%. Analytical data were consistent with that from the prior art.

Example 3

Preparation of 5/6-methoxy-1-benzyloxycarbonyl-2-[[(4-methoxy-3,5-dimethyl-2-pyridinyl)methyl]sulfinyl]-1H-benzimidazole To a solution of 5-methoxy-2-[(4-methoxy-3,5-dimethylpyridin-2-yl)methylthio]-1H-benzimidazole (30 g) in dichloromethane (165 mL) at 0-5° C., under an inert atmosphere, was added meta-chloroperbenzoic acid (0.95 eq) over 10 minutes. The mixture was stirred for 10-15 minutes. To the reaction was added 12% ammonium hydroxide (180 mL). The layers were separated. The organic layer was extracted with 12% ammonium hydroxide (2×180 mL). The combined aqueous layers were washed with toluene (90 mL). To the aqueous layer was added dichloromethane (120 mL) and the mixture was cooled to 0-5° C. The pH was adjusted to pH=8.5-9.5 using 50% aqueous acetic acid. The layers were separated. The aqueous layer was extracted with dichloromethane (2×90 mL). The combined organic layers were washed with brine (30 mL), dried over sodium sulfate, filtered through celite and vacuum distilled to 150 mL to give a solution of 5-methoxy-2-[[(4-methoxy-3,5-dimethylpyridin-2-yl)methyl]sulphinyl]1H-benzimidazole in dichloromethane.

The sulfoxide solution was treated with triethylamine (25.4 mL). The mixture was cooled to 0-10° C. and 95% benzyl chloroformate (13.5 g) in dichloromethane (30 mL) was added while keeping the temperature below 10° C. After stirring for 2-3 hours, water (90 mL) was added. The phases were separated and the aqueous phase was extracted with dichloromethane (60 mL). The combined organic phases were washed with brine (60 mL) and saturated sodium bicarbonate (30 mL) and vacuum distilled to 90 mL. Ethyl acetate (180 mL) was added to the solution and vacuumed distilled to 90 mL. The solution was stirred while 150 mL of heptanes was added at 20-25° C. The suspension was cooled to 0-5° C. and maintained at this temperature for 2-3 hours. The suspension was filtered and the damp cake was pulped in ethyl acetate (30 mL) and heptanes (120 mL) for 1-2 hours. The suspension was filtered, washed with heptanes/ethyl acetate (4/1) (2×30 mL) and dried under vacuum at room temperature to afford 5/6-methoxy-1-benzyloxycarbonyl-2-[[4-methoxy-3,5-dimethyl-2-pyridinyl)methyl]sulfinyl]-1H-benzimidazole. Weight: 25.91 g. Yield: 59%. Ratio of 5- and 6-methoxy products: ~3:2. The analytical data was consistent with the assigned structure.

$^1$H-NMR (300 MHz, CDCl3):

5-Methoxy isomer

δ/ppm=2.19 (3H, s), 2.33 (3H, s), 3.74 (3H, s), 3.77 (3H, s), 4.68 (2H, dd, J=13, 29 Hz), 5.54 (2H, s), 6.96-7.03 (1H, m), 7.39 (1H, m) 7.40-7.42 (2H, m), 7.51-7.56 (2H, m), 7.70 (1H, d, J=9 Hz), 8.05 (1H, s);

6-Methoxy isomer

δ/ppm=2.19 (3H, s), 2.33 (3H, s), 3.74 (3H, s), 3.84 (3H, s), 4.68 (2H, dd, J=13, 29 Hz), 5.53 (2H, s), 6.96-7.03 (1H, m), 7.30 (1H, d, J=2 Hz), 7.40-7.42 (2H, m), 7.51-7.56 (2H, m), 7.76 (1H, d, J=9 Hz), 8.05 (1H, s).

Example 4

Preparation of Amorphous Omeprazole Magnesium Salt

Magnesium metal (0.26 g) was added to methanol (60 mL) and stirred at room temperature for 3-4 hours. To the mixture was added 5/6-methoxy-3-benzyloxycarbonyl-2-[[4-methoxy-3,5-dimethyl-2-pyridinyl)-methyl]sulfinyl]-1H-benzimidazole (10 g) in portions. After stirring for 20-30 minutes the methanol was evaporated to a small volume and ethyl acetate was added, which caused precipitation. The damp cake obtained by filtration was pulped in ethyl acetate for 2-3 hours. The suspension was filtered and cake was vacuum-dried to afford omeprazole magnesium salt. Weight: 7.0 g. Purity: 99.5% by HPLC.

As many changes can be made to the preferred embodiments of the invention without departing from the scope thereof, it is intended that all matter contained herein be considered illustrative of the invention and not in a limiting sense.

The invention claimed is:

1. An optically active compound of formula (III):

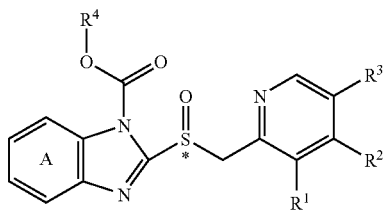

wherein ring A is a benzene ring optionally having 1 to 3 substituent(s), which may be the same or different, are each independently selected from (a) a halogen atom, (b) a cyano, (c) a nitro, (d) an alkyl optionally having 1 to 3 substituent(s) selected from a halogen atom, a $C_{1-6}$ alkoxy, a $C_{1-6}$ alkoxy carbonyl and a carbamoyl, (e) an alkoxy optionally having 1 to 3 substituent(s) selected from a halogen atom, a $C_{1-6}$ alkoxy, a $C_{1-6}$ alkoxycarbonyl and a carbamoyl, (f) an aryl, and (g) an aryloxy, $R^1$, $R^2$ and $R^3$ are each a hydrogen atom; an alkyl group optionally having 1 to 3 substituent(s) selected from a halogen atom, a $C_{1-6}$ alkoxy, a $C_{1-6}$ alkoxycarbonyl and a carbamoyl; an alkoxy group optionally having 1 to 3 substituent(s) selected from a halogen atom, a $C_{1-6}$ alkoxy, a $C_{1-6}$ alkoxycarbonyl and a carbamoyl; or a di-$C_{6-14}$ arylamino, $R^4$ is an aryl or aralkyl group, and

* is an asymmetric center or their pharmaceutically acceptable alkali and alkaline earth salts.

* * * * *